United States Patent
Creighton, IV et al.

(10) Patent No.: US 6,330,467 B1
(45) Date of Patent: Dec. 11, 2001

(54) EFFICIENT MAGNET SYSTEM FOR MAGNETICALLY-ASSISTED SURGERY

(75) Inventors: Francis M. Creighton, IV, St. Louis; Andrew F. Hall, St. Charles; Roger N. Hastings, Maple Grove, all of MO (US); Rogers C. Ritter, Charlottesville, VA (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/287,397

(22) Filed: Apr. 6, 1999

Related U.S. Application Data

(60) Provisional application No. 60/118,959, filed on Feb. 4, 1999.

(51) Int. Cl.[7] ................................................ A61B 5/05
(52) U.S. Cl. ................................................... 600/407
(58) Field of Search ........................... 600/9, 10, 13, 600/14, 407

(56) References Cited

U.S. PATENT DOCUMENTS

| | | | |
|---|---|---|---|
| 4,994,015 | * | 2/1991 | Cadwell ................................ 600/13 |
| 5,667,469 | * | 9/1997 | Zhang et al. ......................... 600/9 |
| 5,772,594 | * | 6/1998 | Barrick ................................ 600/407 |
| 6,042,531 | * | 3/2000 | Holcomb .............................. 600/13 |
| 6,099,459 | * | 8/2000 | Jacobson .............................. 600/13 |

OTHER PUBLICATIONS

A New Magnet System for 'Intravascular Navigation'*† Shyam B. Yodh, M.D., & biol. Engng. vol. 6, pp. 143–147.

* cited by examiner

*Primary Examiner*—William E. Kamm
(74) *Attorney, Agent, or Firm*—Harness Dickey & Pierce

(57) ABSTRACT

A system for magnetically assisted surgery includes a magnetic support structure, a patient support structure and a magnet having at least four poles attached to the magnetic support structure so that the magnet provides a near-field magnetic field in an operating region of a patient supported by the patient support structure. The magnet is moveable so that the direction of the magnetic field lines in the operating region is adjustable. The magnet may include a pair of essentially semicircular half-segments permanently magnetized and joined in an extremely stable disk configuration. The magnetic field and gradient field provided by the magnet is such that movement of the disk in one plane combined with rotation of the disk is sufficient to orient the magnetic field during surgical use, thereby reducing interference to medical imaging devices needed during surgery. An example of a medical delivery device that may be used for surgery in conjunction with this system is a flexible endoscope or catheter having a series of magnetically permeable rings.

14 Claims, 9 Drawing Sheets

EFFICIENT MAGNET SYSTEM FOR MAGNETICALLY-ASSISTED SURGERY

CROSS REFERENCE TO RELATED APPLICATION

This application claims priority of U.S. provisional patent application Ser. No. 60/118,959, filed Feb. 4, 1999.

FIELD OF THE INVENTION

This invention relates to systems for magnetically-assisted surgery and more particularly to systems for producing the magnetic fields required to guide surgically implanted magnetic medical devices.

BACKGROUND OF THE INVENTION

Several magnet systems to provide guidance for magnetic medical devices for navigation within a patient have been devised or are under development. An example of such a system is disclosed in commonly assigned app. Ser. No. 09/189,633, "Articulated Magnetic Guidance System," which is hereby incorporated by reference in its entirety. A device disclosed therein includes a bed, a bed articulation system, a pair of x-ray sources, a coil or magnet articulation system, and an optional pair of additional magnets. The magnet articulation system comprises an articulation support, servo control mechanisms to provide movement of a coil or a permanent magnet along an arcuate arm both through a polar angle and in a radial direction. Optionally, the entire arm may also be pivoted through an azimuthal angle. The arm itself may comprise a track and gimbal assembly. Additional embodiments described in the referenced application include one in which the arm itself is moveable via an articulation support, another in which the magnet or coil is mounted on a pivotable ring support, and another in which the magnet or coil is mounted as an effector on a robotic arm. In the latter embodiment, it is desirable for the effector and all other parts of the robotic arm to be provided with exclusion zones to prevent accidental contact with a patient, with medical personnel, and, of course, with other items that might be damaged by such contact.

Other magnetic systems that provide guidance for magnetic medical devices within a patient are disclosed in commonly assigned app. Ser. No. 09/211,723, filed Dec. 14, 1998, "Open Field System for Magnetic Surgery," which is also incorporated by reference in its entirety. A plurality of magnets are configured and arranged to provide a magnetic field effective within an operating region of a patient to navigate a magnetic medical device within the operating region while providing access to the patient for imaging and other purposes. A single magnet is arranged and configured to provide a magnetic field along at least one of a plurality of oblique axes extending through the operating region. One or more magnets are arranged and configured to provide a magnetic field along each of the other of the oblique axes. The magnetic fields generated by the magnets are effective to controllably navigate the magnetic medical device within substantially the entirety of the operating region. A preferred embodiment of the system described in this reference comprises three magnets in three mutually perpendicular planes, arranged so that their axes at least converge and more preferably intersect in the operating region. The magnets are arranged in an open configuration, so that the patient typically does not have to extend through a magnet coil to reach the operating region. In a preferred embodiment, the magnets comprise coils that are fixed with respect to one another in a generally downwardly facing hemispherical shell.

Still other magnetic systems providing guidance for magnetic medical devices navigated within a patient are disclosed in commonly assigned Provisional app. Ser. No. 60/095,710, filed Dec. 14, 1998, "Method and Apparatus for Magnetically Controlling Catheters for body Lumens and Cavities," which is also incorporated by reference in its entirety. The apparatus of the invention disclosed therein generally comprises a magnet system for applying a magnetic field to a magnet-tipped distal end of a medical device. The magnetic field provides a field that can navigate, orient, and hold the distal end of the medical device in the body. The apparatus also includes a computer for controlling the magnet system. Imaging devices connected to the computer provide images of the body part through which the catheter is being navigated. Displays are provided of these images. A controller connected to the computer has a joystick and a trigger to enable a user to input points on the displays for two-point and three-point navigation. The magnet system itself is preferably a set of electromagnetic coils that can be disposed around the body part to create a magnetic field of variable direction and intensity. Magnet systems suitable for such use are disclosed in U.S. Pat. No. 4,869,247, issued Sep. 26, 1989, "Video Tumor Fighting System," and U.S. Pat. No. 5,125,888, issued on Jun. 30, 1992, entitled "Magnetic Stereotactic System for Treatment Delivery," the disclosures of both of which are also incorporated by reference in their entirety.

In the commonly assigned application entitled "Device and Method for Specifying Magnetic Field for Surgical Applications," app. Ser. No. 09/020,798, filed Feb. 9, 1998, and which is hereby incorporated by reference in its entirety, six normally conducting or superconducting coils are arranged in a rectangular box or helmet. With the Z-axis defined in the direction of the axial component of the head, the X- and Y-coil axes are rotated 45° from the sagittal plane of the head. Biplanar fluoroscopy cameras linked to a real-time host system are provided. Both cameras are calibrated to the six-coil host helmet design, in which three pairs of opposing coils on mutually perpendicular axes are provided. X-ray generators are also provided for the cameras.

In yet another commonly-assigned application entitled "Method and Apparatus Using Shaped Field of Repositionable Magnet to Guide Implant," app. Ser. No. 09/020,934, filed Feb. 2, 1998, and which is herein incorporated by reference in its entirety, an apparatus comprising a moveable magnet assembly having a plurality of fiducial marks is disclosed. In an exemplary embodiment, the magnet assembly may be a gantry supporting either a strong permanent magnet or a superconducting electromagnet, although a strong permanent magnet may require additional articulation to compensate for its lack of current control and magnitude. The magnet assembly may be automatically controlled to provide the needed orientation, location and coil current required to align its magnetic field with the desired motion of a magnetic object to be guided. Localizers and camera-like sensors are provided to detect the fiducial marks on the magnet assembly, and additional fiducial markers may be placed on the patient's body. Medical imaging devices are used to display the location of the magnet relative to the volume of interest in the patient and the location of the implant. Various means are provided for moving the magnet.

Each of these devices and methods provides some success in being able to provide magnetic field orientations in all directions in sufficient strength for the intended applications. Nevertheless, even with specially designed systems, it is still difficult to completely avoid interference with the imaging system while achieving full functionality of the magnetic guidance system. In many of the above systems, this difficulty becomes apparent in the requirement to provide limitations in the movements of one or more large magnets or their supporting structures, or in limitations imposed on movements and positioning of an imaging system relative to the magnet system. In addition, the systems designed to date, including many of the above, have been quite large and expensive, or are restricted in purpose and application.

The magnets used in magnetic navigation are typically superconducting electromagnets which provide controllable, strong magnetic fields. One drawback of superconducting electromagnets is the cryogen system required to keep the coil at the approximately 4° K needed to safely maintain the superconducting state of the coil. The size and weight of the cryogen system makes it difficult to support and move the superconducting electromagnetic coil and also restricts the orientations in which the coil can be positioned. While substantial progress has been made in the design of cryogenic systems, there are limits on the position and orientation of the dewar for the cryogen, which limits the orientations in which the associated coil may be placed. The size of the cryogen system also restricts where the coil can be positioned relative to the patient.

It would therefore be desirable to provide a relatively inexpensive system for magnetically assisted surgery that could produce a magnetic field in any orientation and at sufficient strength for use in medical applications. It would also be desirable if the system could provide field lines through a given procedure point in space (i.e., the location of the magnetic medical device) that could be easily and safely changed with a minimum of articulation of the magnet, so that the effect of the various exclusion zones in an operating region could be minimized. It is also desirable to provide such a magnet system where the magnet is compact and capable of being moved in any orientation relative to the patient to maximize the freedom of navigation within the patient.

SUMMARY OF THE INVENTION

According to the method of this invention an element that is responsive to a magnetic field is controlled within a patient's body by the application of at least two different magnetic fields, each field having a different angular relationship between the field direction and the gradient. This can be conveniently done by translating or rotating a magnet, such as a permanent magnet or an electromagnet, and in particular a multipole magnet such as a quadrupole magnet. Relatively small translations or rotations of multipole magnets can result in substantial changes in field direction and/or the angular relationship between the field direction and gradient.

The system for magnetically assisted surgery of a patient of this invention comprises a magnet support structure, a patient support structure, and a multipole magnet attached to the magnet support structure so that the magnet provides a near-field magnetic field in an operating region within a patient supported by the patient support structure. The magnet is moveable to alter the direction of magnetic field lines in the operating region of the patient. The magnet is preferably a quadrupole magnet, and may be a permanent magnet.

If the magnet is a permanent quadrupole magnet, it is preferably cylindrical, comprising a pair of essentially semicircular segments joined so that the segments attract each other strongly in a highly stable arrangement. This arrangement would provide, in a region near a face of the magnet disk, a magnetic field essentially parallel to the face of the magnet disk, along the axis of the magnet. The magnet may be mounted so that it can be rotated on its axis and/or translated in one or more radial directions. A medical imaging system may also be provided and configured to provide a medical image of the operating region of a patient.

In accordance with a second aspect of the invention, a system for magnetically assisted surgery of a patient comprises a magnetic medical device configured to be implanted in a patient, a patient support structure, a magnet support base, and a magnet assembly adjustably supported on the support base and positionable thereon to provide a magnetic field of specified magnitude and direction and having a transverse gradient at the location of the magnetic medical device within the patient supported by the patient support structure. The magnet assembly may comprise a computer-controlled robotic arm having a magnetic effector, and the system may further comprise a medical imaging device configured to provide a relative location and orientation of the magnetic medical device in the patient and of the magnet assembly. The magnet assembly may itself comprise a permanent magnet, an electromagnet, or a superconducting electromagnet.

In the case of a superconducting electromagnet, in accordance with the present invention the superconducting coil preferably includes a mechanical refrigeration system instead of a conventional cryogen cooling system. The refrigeration system is more compact, less expensive to operate, and allows greater maneuverability of the superconducting coil relative to the patient.

In some applications it is important to have a field in a direction approximately perpendicular to the "pulling" direction, i.e., the gradient direction. In some instances it would further be desirable to controllably change the relationship between the gradient direction and the field direction. One way of doing this efficiently is to use a multipole magnet, such as a quadrupole magnet. In such magnets, simple translation can change the field direction 90° while, since the gradient direction remains unchanged, changing the relationship between the field direction and the gradient direction. Another way of doing this efficiently is to use a simple magnet, and rotate it to use the side field. A simple magnet can be less expensive and stronger for a given weight than a multipole magnet, but there are occasions where the rotation required of a simple magnet might make the articulation more interfering with imaging and other medical apparatus in the surgical field.

The apparatus and method of this invention can thus provide for applying a directing magnetic field at any desired angle to a magnetic medical device within an operating region in a nearby patient, while simultaneously applying a pulling gradient in an essentially transverse direction to the orientation of the magnetic field.

The apparatus and method of this invention can also provide a method and apparatus for performing surgery on a patient by directing a magnetic medical device, such as a catheter or endoscope having a magnetic or magnetically permeable tip, in a direction perpendicular to the magnetic field. Thus, the magnetic medical device axis is easily oriented, even with modest or weak magnetic fields.

The apparatus and method of this invention can also provide an external magnet system for magnetically assisted surgery that will provide an orienting field and transverse gradient for stable and reliable movement of a magnet medical device.

The apparatus and method of the invention can also provide an external magnet system for magnetically assisted surgery using a magnetic medical device, in which the direction and strength of the magnetic force on the magnetic medical device may readily be controlled by a surgeon.

Finally, the apparatus and method of this invention can provide a magnet system for magnetically assisted surgery that minimizes the limiting effect of exclusion zones on the ability of the magnet system to provide magnetic fields of selected direction and strength within.

The manner in which these and other features of the invention are achieved will become apparent to one skilled in the art upon study of the accompanying figures and description.

BRIEF DESCRIPTION OF THE DRAWINGS

Although the figures are intended to be illustrative, it should not necessarily be assumed that the figures are drawn to scale. Corresponding reference numerals indicate corresponding parts throughout the several views of the drawings.

DETAILED DESCRIPTION OF THE PREFERRED EMBODIMENT

Figure 1:
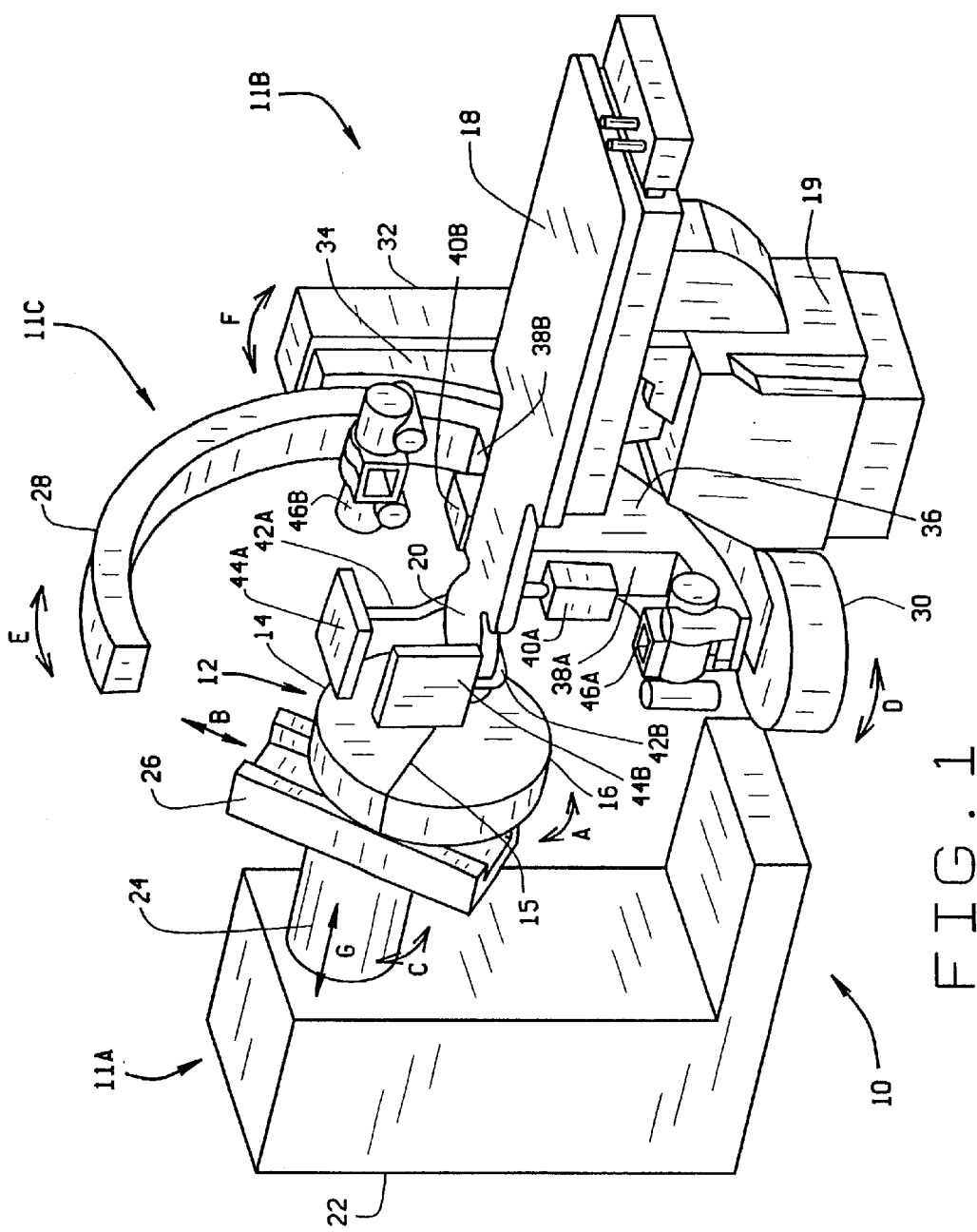
FIG. 1 is a perspective view of an embodiment of a system for magnetically assisted surgery in accordance with the invention.

FIG. 1 is a drawing of a system 10 for magnetically-assisted surgery. The system generally comprises two sections; a magnet assembly 11A and a patient support 11B. Magnet assembly 11A comprises a magnet 12 that is located or brought into proximity with an operating support region 20 of patient support 11B.

Magnet assembly 11A comprises a magnet 12, preferably having more than two poles, and which is preferably a quadrupole magnet in the form of a disk or cylinder having two semi-cylindrical segments 14 and 16 joined magnetically at a seam 15 coincident with a diameter of the cylinder. Each of the half segments 14 and 16 are magnetized in different directions so that the two segments attract each other with great force when assembled into a disk to thereby form a very stable mechanical system. While other forms of quadrupole magnets can provide similar results, the form of magnet 12 shown in FIG. 1 and which is described in more detail below provides remarkable simplicity and efficiency. Although a quadrupole magnet is believed preferable, magnets or assemblies of magnets having more than four poles could be substituted for magnet 12 within the scope of the invention.

Figure 2:
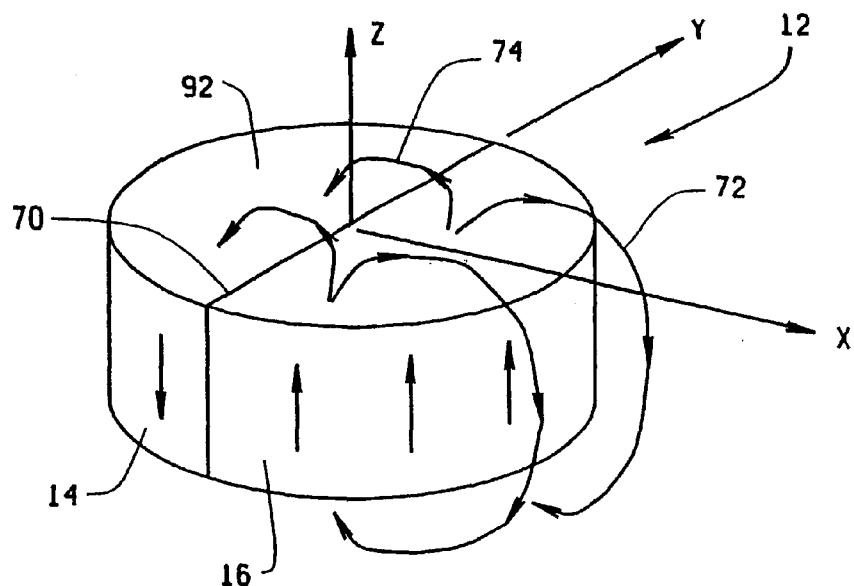
FIG. 2 is a perspective view of the magnet assembly of FIG. 1.

FIG. 2 shows how the half segments of the magnet cylinder 12 are magnetized to provide advantages in accordance with this invention. The axis of the cylinder 12 is taken as the Z axis, while the seam 70 that joins the half segments 14 and 16 arbitrarily defines a Y direction. The X direction is taken as being perpendicular to the Y direction and the Z axis. On one side of seam (15)70, half segment 14 of magnet disk 12 is magnetized in the −Z direction, while half segment 16 of magnet 12 is magnetized in the +Z direction. As indicated above, there is a considerable magnetic force holding the two half segments 14 and 16 together along seam (15)70, making magnet disk 12 a very stable structure.

FIG. 2 also shows a few of the magnetic field lines 72, 74 of magnet 12, the arrangement of which provide special features of the system. It is known that the distant field strength of a quadrupole falls off with distance by one power greater than that of the dipole. Therefore, one might expect that quadrupole magnets would be less useful than dipole magnets in surgical applications, where large magnetic fields are frequently required. However, for medical and surgical applications, the system described herein takes surprising advantage of the magnetic field lines in the near and transition fields of the quadrupole magnet 12.

Figure 3A:
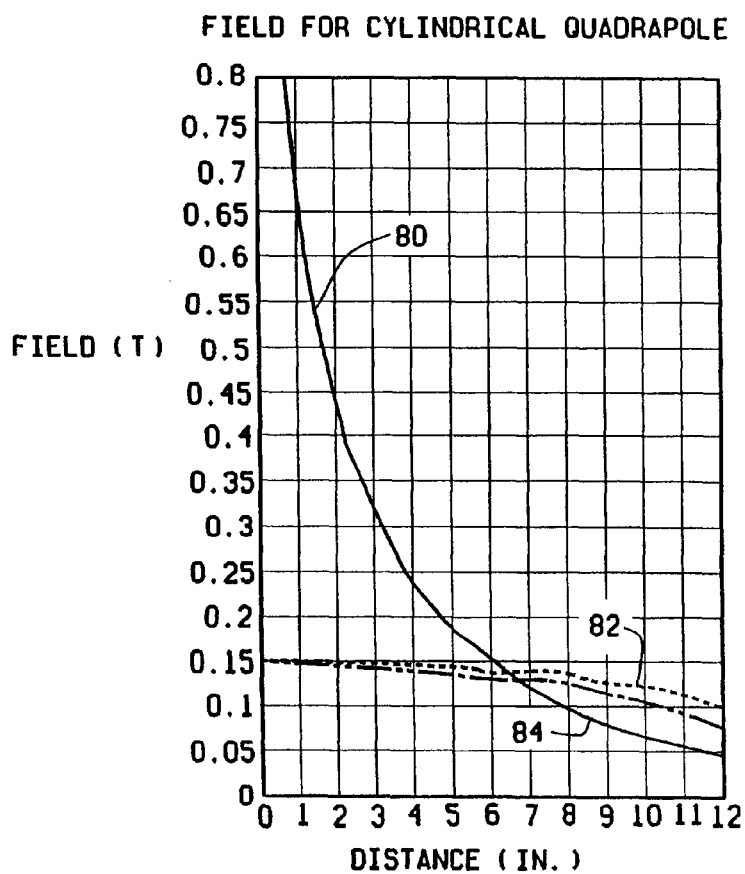
FIG. 3A is a graph showing relationships of magnetic field strength and distance along the axes of a cylindrical quadrupole magnet.
Figure 3B:
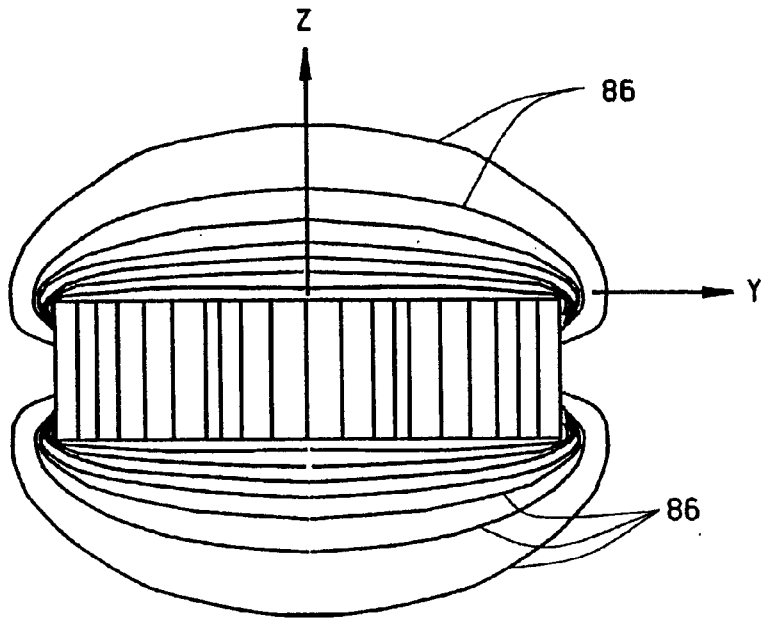
FIG. 3B is a graph showing contours of equal field strength when the magnet of FIG. 2 is viewed from the −X direction.

To provide an effective magnetic field for surgical applications, quadrupole magnet 12 may preferably comprise a NdFeB magnet of 44 MgOe maximum energy, having a radius of 12.39 inches and a thickness of 6.20 inches. In this case, quadrupole magnet 12 would weigh about 800 pounds and could be permanently magnetized to achieve a field strength along the Z axis of about 0.15 Tesla at 6 inches from its face 92. FIG. 3A is a graph of the magnetic field strength in Tesla calculated for this cylindrical quadrupole magnet 12 along the three axes of the magnet; line 80 shows the strength along the Z axis, and lines 82 and 84 show the strength along the X and Y axes, respectively. Contours 86 of equal field strength when viewing magnet 12 towards the −X direction are illustrated in FIG. 3B, while contours 88 of equal field strength when viewing magnet 12 towards the +Y direction are illustrated in FIG. 3C.

Figure 3C:
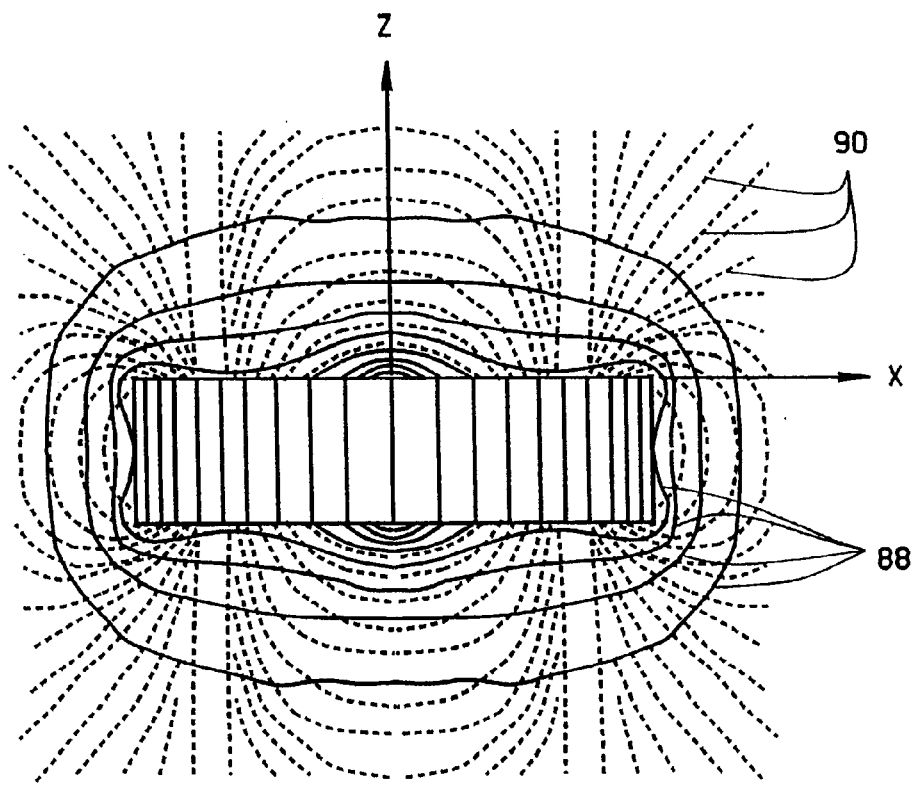
FIG. 3C is a graph showing contours of equal field strength when the magnet of FIG. 2 is viewed from the +Y direction.

The multitude of small arrows 90 in FIG. 3C represents magnetic field directions on a grid of points. The arrangement of field line directions crossing the Y-Z plane (the plane of seam 70) are parallel to face 92 of the magnet as seen in FIG. 2. Therefore, a rotation of magnet 12 about the Z axis will change the magnetic field direction at any point on the Z axis while maintaining the same strength. It is thus possible to rotate the magnetic field direction along the Z-axis by 360° or any portion thereof without an accompanying translation of quadrupole magnet 12. On the other hand, translation of the quadrupole magnet 12 along the X axis by slightly over half of its radius will turn the magnetic field so that it is directed along the −Z direction. The same translation along the −X axis will turn the field so that it is oriented in the +Z direction. It will thus be apparent that complete control of magnetic field direction in an operating region of a body for medical and surgical applications can be achieved by, at most, two translations and one rotation, or two rotations and one translation of quadrupole magnet 12. Such an operating region of a body could include a person's head, as for magnetically assisted brain surgery. Although not shown in the figures, it may be advantageous in some applications to mount magnet 12 so that its Z axis may also be tilted. In use, the patient's operating region will be in the near field of magnet 12.

Figure 4:
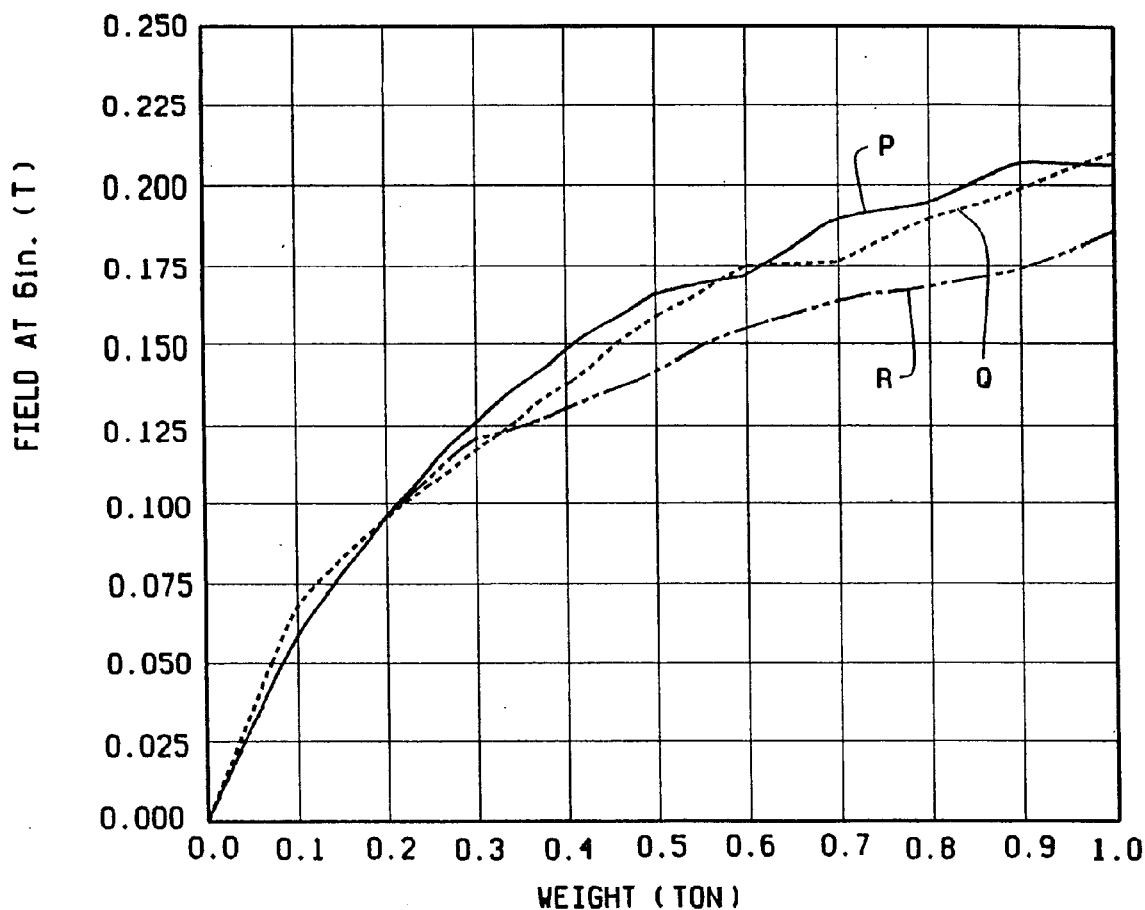
FIG. 4 is graph showing the relationship of the calculated weight of the magnet of FIG. 2 to its calculated magnetic field at a distance six inches from its face.

Because cost and navigation efficiency are partly determined by size and weight, FIG. 4 provides a plot showing the relationship of the calculated weight of magnet 12 to its calculated magnetic field at a distance 6 inches from its face. The plot has been calculated for three different aspect ratios (i.e., the ratio of radius to thickness). Line P is for an aspect ratio of 1.0; line Q is for an aspect ratio of 2.0; and line R is for an aspect ratio of 4.0.

Referring again to FIG. 1, magnet 12 is preferably rotatably mounted on a track 26. This mounting allows two independent movements of magnet 12, one being a rotation on the axis of the magnetic disk 12 shown by arrow A, and the other being translation along track 26 as indicated by arrow B. Preferably, track 26 itself is also rotatable about an axis as indicated by arrow C. This additional rotation may be provided by mounting track 26 on a shaft 24 that is rotatably mounted on the support base 22 of magnet assembly 11A. Shaft 24 may also be slidable along its axis to thereby provide another direction of motion that permits magnet 12 to be withdrawn from proximity to the operating region of the patient. This motion is indicated by arrow G in FIG. 1.

The embodiment of magnet assembly 11A in FIG. 1 thus provides a quadrupolar magnet 12 that is or that may be brought into close proximity with an operating region of a patient. Quadrupole magnet 12 may be subject to a plurality of rotational and translational movements to provide differing magnetic field orientations in the operating region. Translation in three dimensions (including withdrawal from the operating region) is provided in the embodiment of FIG. 1. In other embodiments, it may be possible to mechanically tilt the axis of the magnet with respect to the operating region. Although tilting may be desirable in some operating situations, it is not necessary to practice the invention.

Magnet assembly 11A may comprise a robotic support manipulator to provide the rotation and translation of magnet 12, and may optionally also provide tilting of the Z axis of magnet 12. Because of the weight of magnet 12 and for other reasons, as well, robotic control is preferable to full manual movement of magnet 12, although manual control is both possible and contemplated within the scope of the invention. The movements required of the robotic manipulator are those that are required to make possible the movements of magnet 12 as described herein. Robotic manipulators are well-known in the art, and the design of servo mechanisms to provide the needed movements of magnet 12 would present no special difficulties to one skilled in that art. Such servo mechanisms could be manually controlled by a surgeon viewing real-time medical images of the operating region of a patient, or could be automatically controlled by a computer interpreting such images. If manually controlled, a computer could provide assistance by displaying medical images of the operating region of the patient, showing the magnetic delivery vehicle (MDV) or magnetic seed in the patient with other useful information superimposed or adjacent to this image. This other information could include a desired path of the MDV or magnetic seed and the magnetic field lines or gradient of magnet 12.

FIG. 1 illustrates a patient support essentially identical to that described in copending application Ser. No. 09/211,723, filed Dec. 14, 1998, and incorporated by reference above. Patient support 11B comprises a bed 18 that is supported at a convenient operating level by a base support 19. Bed 18 includes a region 20 that is or can be brought into proximity with magnet 12. (Although it is contemplated that the magnet 12 will be moveable, movement of the operating region of a patient relative to magnet 12 may alternately, in some circumstances, be accomplished by moving the bed 18 supporting the patient.) Also provided is a rotating pivot or swiveling support 30 on which is attached an imaging assembly 11C comprising a base frame 32, arcuate support 34, and arcuate section 28. Part of imaging assembly 11C may comprise any suitable, commercially available C-arm assemblies, such as those made by General Electric Co. of Syracuse, N.Y, however, it is not required that the "arcuate" section be in the shape of an arc. Because commercially available C-arm assemblies usually are this shape, however, it is convenient to use this terminology. Support 30 need not be mounted or free-standing on a floor, as shown here. Some other mounting possibilities include attachment of support 30 to an extension of base support 19 of patient support 11B, or to an extension of support base 22 of magnet assembly 11A. Mountings that do not require movements of imaging assembly 11C that interfere with the attached imaging apparatus described below when magnet 12 is repositioned are preferable.

Arcuate section 28 supports one or more X-ray or fluoroscopic tubes 46A and 46B for use in providing a medical image of the operating region of the patient supported at region 20 of bed 18. Thus, each of the tubes 46A and 46B have their beams aimed at corresponding imaging plates 44A and 44B through this region. Preferably, imaging plates 44A and 44B are held in place by imaging plate supports 42A and 42B, respectively, which are separate supporting arms. The position of these plates may be adjusted somewhat by moving blocks 40A and 40B, respectively, which are configured to slide (such as on tracks, not shown in FIG. 1), over surfaces 38A and 38B of a pie-shaped portion 36 of arcuate support 28.

Figure 5:
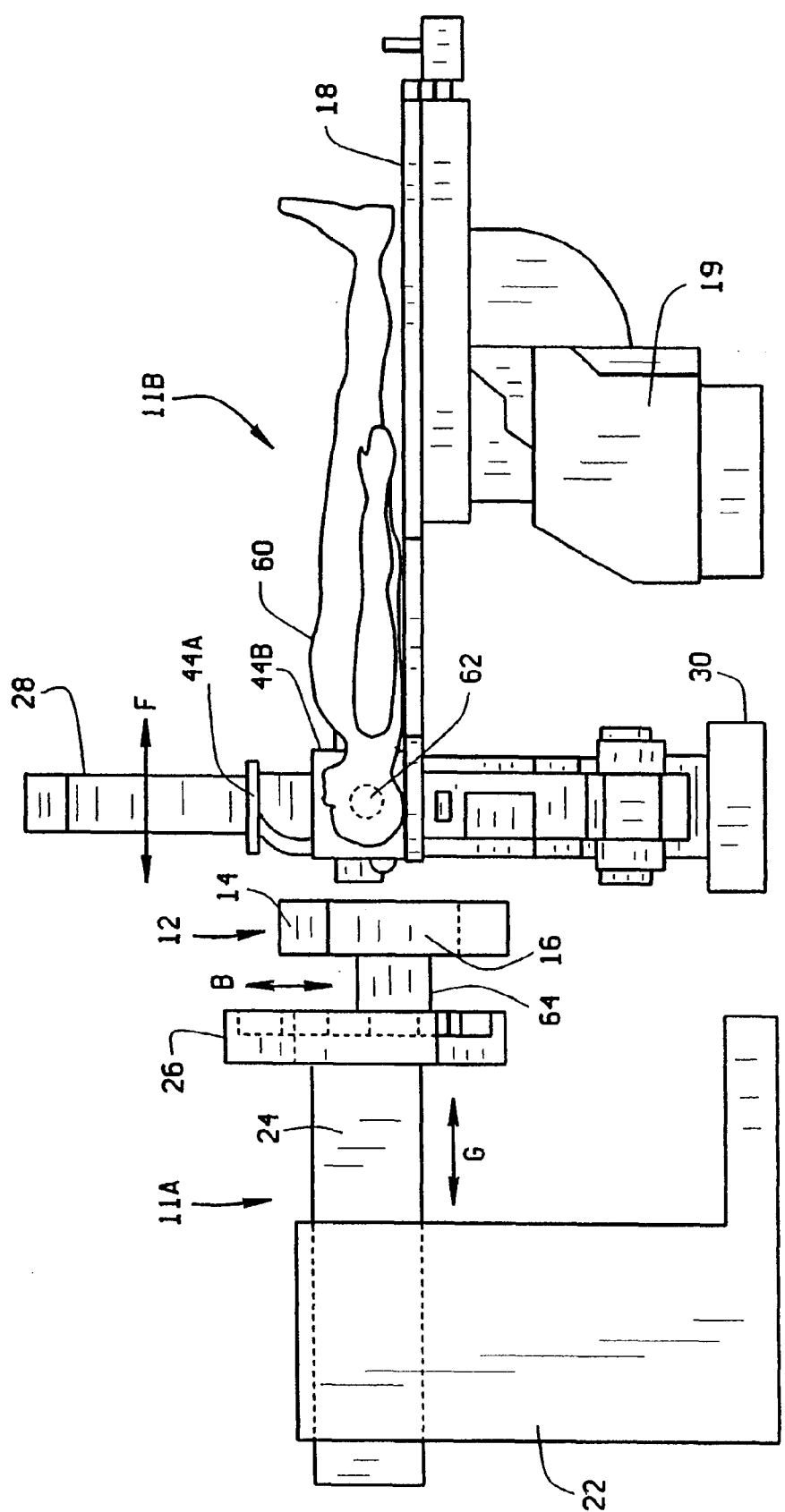
FIG. 5 is side view of the apparatus shown in FIG. 1, showing some of the movements of both the magnet assembly and the patient support relative to an operating region of a patient.

Some of the pivoting and movement mechanisms of the C-arm and imaging assembly 11C are not shown in FIG. 1, but are shown and described in app. Ser. No. 09/211,723. Briefly, arcuate section 28 is configured to provide various views of an operating region of a patient by pivoting at swivel support 30 (shown by arrow D), partial rotation around another pivot (as shown by arrow F, along an axis preferably perpendicular to the pivoting axis at 30), and by partial rotation of the entire arcuate section 28 around a central point, as indicated by arrow E. Each movement of arcuate section 28 also causes the imaging tubes 46A and 46B and their respective imaging plates to move correspondingly relative to the operating region of the patient, which is not operatively coupled to these C-arm movements. Thus, various views of the operating region are available. Some of the movements of both magnet assembly 11A and patient support 11B may also be seen in FIG. 5, which also shows where an operating region 62 of a patient 60 would be situated in relation to the parts of the inventive apparatus. It will be recognized that the views provided by the imaging devices can provide the relative locations of magnet assembly 11A, a medical delivery device in a patient 60, and an operating region of the patient 62.

It will be observed that movement of the arcuate section 28 and the objects attached to it result in physical exclusion volumes being created. These are regions of space that are or may be occupied by the moving components, and that must therefore be avoided by movements of the magnet 12 or magnet assembly 11A. If the physical exclusion volumes are not respected, physical interference between the components of the system occur. It may also be useful to consider magnetic as well as physical exclusion regions. Magnetic exclusion regions are regions from which, taking into account the movement of magnet 12, magnetic objects or objects that may be adversely affected by magnetic fields should be excluded. Thus, it may be desirable to avoid placing some types of imaging plates 44A and 44B within a region of high field strength of magnet 12. However, because of the relatively small size of quadrupole magnet 12 and the requirement of only limited rotational and translational movement, both its physical and magnetic exclusion zones are advantageously quite small. Additionally, because magnet 12 is a quadrupole magnet, the magnetic exclusion zone is smaller than might otherwise be the case, because the magnetic field generally drops off more quickly with distance for such magnets than with the dipole magnets and solenoids previously used. (Similar advantages may be obtained with magnets having more than four poles.)

Figure 6:
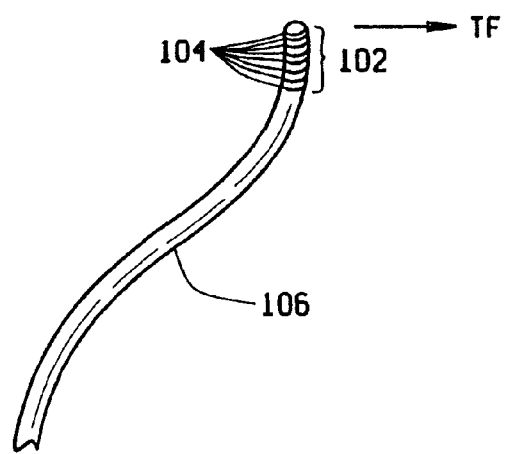
FIG. 6 is an illustration of a magnetic medical device that may be introduced into a patient and used in conjunction with the magnetic surgical systems of this invention.

The inventive system described herein is intended for use in magnetically assisted surgery. For example, it may be used to guide a tiny magnet on the end of a catheter or guide wire that is magnetically navigated into an aneurysm in the brain. A magnetic medical device 102, as illustrated in FIG. 6, may be introduced into an operating region 62 of a patient 60 in accordance with this invention. Magnetic medical device 102 may comprise a series of magnetically permeable rings 104. These rings may be mounted on a slightly flexible rod 106, such as a catheter or endoscope. The individual moments of the rings are induced to be along the direction of the magnetic field of magnet 12, and this orientation is not altered by the gradient of the field. Instead, the gradient and the direction of the field may be used in a complementary way so that the axis 108 of the magnetic medical device is easily oriented, even with the application of modest or weak magnetic fields from the external magnet 12. At the same time, the transverse gradient applies a transverse force TF on the moment of the system.

Magnet assembly 11A and patient support 11B as shown and described herein are physically separate assemblies, but it should be clear that this is not a requirement of the invention. It is also not necessary that patient support 11B be in the form shown here. Any form of supporting structure suitable for holding or supporting an operating region of a patient may be used, possibly including a floor in an emergency, with suitable modification of either or both magnet assembly 11A and imaging assembly 11C so that the magnet may be appropriately positioned and the operating region properly imaged. In the claims appended below, it should be understood that a magnet support structure and a patient support structure need not be physically separate assemblies, and that, unless explicitly stated otherwise, the magnet support structure and patient support structure may comprise different portions of a single structure.

In alternate embodiments, a magnet may be attached to a flexible or articulated arm that is attached to the ceiling, rather than to a support structure such as shown in FIG. 1 that is attached to or supported by the floor. A ceiling mounted assembly would avoid congestion at the floor area of the patient. Moreover, the flexible or articulated arm may be designed to allow easy manual or adjustment of the position and angle of the magnet assembly. Alternately, the ceiling supported assembly could be robotically controlled.

In another alternative embodiment, the transverse magnitude and gradient fields may be generated by an electromagnet rather than a permanent magnet. It is a general characteristic of coil systems having standard symmetries (i.e., that are symmetric about the coil axis and symmetric with respect to a center, equatorial plane of the coil) that in regions in and near the equatorial plane, both inside and outside the coil, a magnetic field exists that is parallel to the coil axis, while at the same time a transverse gradient of the field is perpendicular to the axis. For example, a single circular turn of wire in a plane has such a field and gradient relationship. However, for such a coil, the region inside or outside the coil at which this relationship occurs is too narrow to be useful. Attempts to use such a coil to magnetically assist a surgical procedure employing a magnetic medical device will be subject to error due to operator inaccuracy.

Appreciable regions around a long solenoid coil (with either normally conducting or superconducting turns) will have an essentially transverse relationship of field and gradient. However, the field and gradient will be relatively weak for a given number of ampere-turns of the coil. However, upon recognizing the advantages of providing the transverse field and gradient relationship in accordance with this invention, one skilled in the art would be able to optimize the design of a coil for use in conjunction with the invention. Such a coil would have a sufficiently large region in which the required relationship exists, at a suitable distance from the coil for use in a desired surgical application. Permanent magnets may also be designed with similar characteristics, although different mathematical tools may be required. The quadrupole magnet 12 described in detail above is one particularly simple and advantageous permanent magnet design in accordance with this invention.

Figure 7:
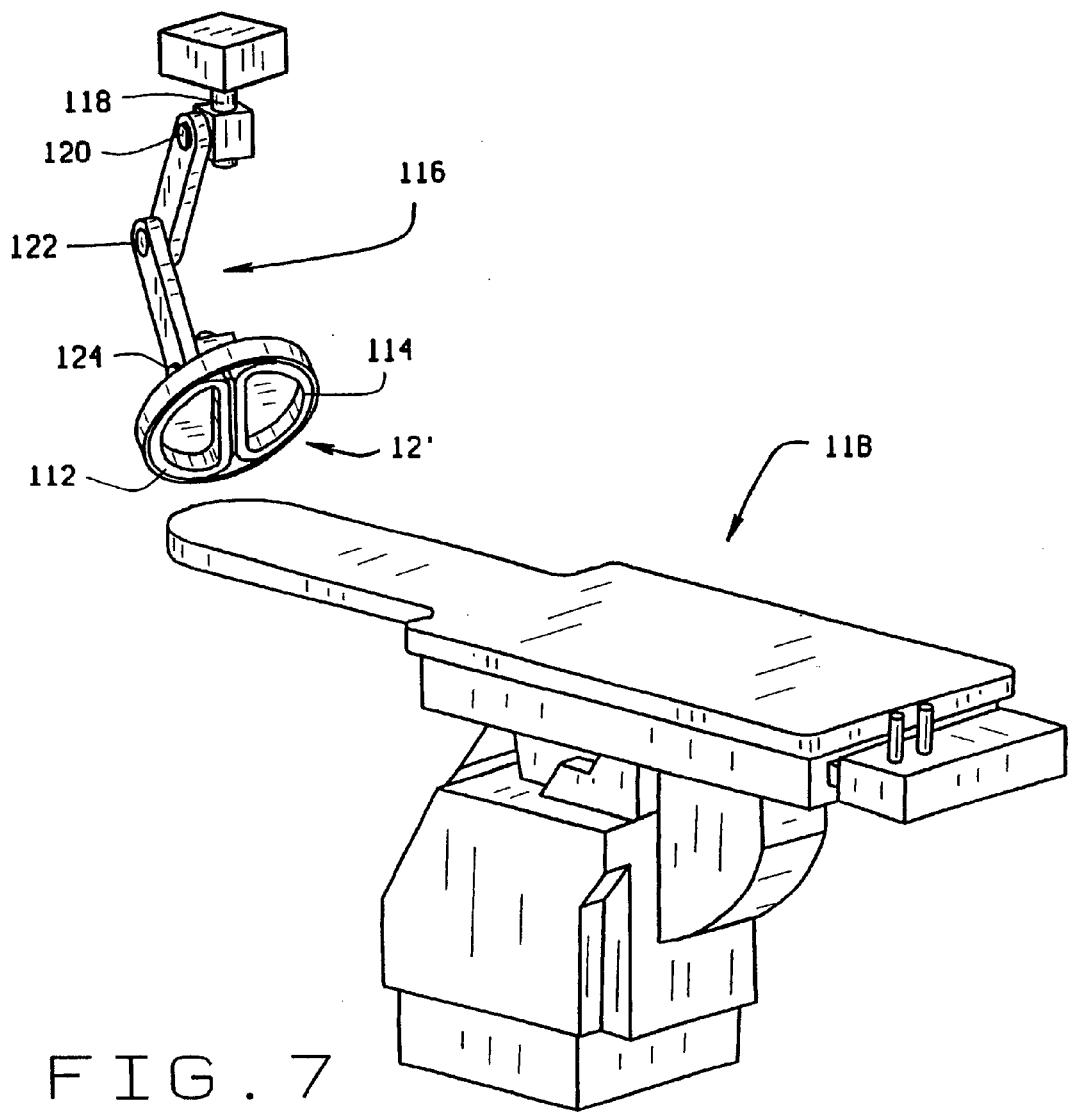
FIG. 7 is an isometric, schematic illustration of an embodiment of the system for magnetically assisted surgery employing a quadrupole electromagnet.

Notwithstanding the above remarks, it is possible to configure two or more (preferably superconducting) electromagnets to achieve many of the advantages of the permanent quadrupole magnet 12 discussed above, as well as some additional advantages. Such a configuration is represented isometrically (and somewhat schematically) in FIG. 7. Referring to FIG. 7, quadrupole magnet 12' comprises a pair of preferably D-shaped coils 112, 114 mounted at an end of an articulated arm 116. The straight sections of coils 112 and 114 are preferably closely adjacent to one another, as shown. Articulated arm 116 has a number of joints exemplified by 118, 120, 122, 124. The joints provide sufficient articulation to position and rotate quadrupole magnet 12' around an operating region of a patient placed on patient support 11B. An articulated arm 116 suitable for this purpose will be found in commonly assigned app. Ser. No. 09/189, 633, filed Nov. 10, 1998, entitled "Articulated Magnetic Guidance Systems and Devices and Methods for Using Same for Magnetically-Assisted Surgery," which is hereby incorporated by reference in its entirety. Movement of articulated arm 116 may be manually controlled, or more preferably, robotically controlled, such as by computer-controlled servo systems, which may preferably be coordinated with a medical imaging system as well as one or more visual display systems and input systems to assist a surgeon guiding a magnetic implant influenced by quadrupole magnet 12'. Many of these systems are not shown in FIG. 7, but it will be understood that at least a medical imaging system such as one similar to that shown in FIG. 1 and described in conjunction therewith would normally be present and would be used during surgery.

Figure 8A:
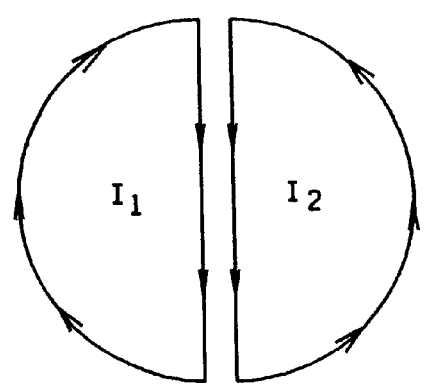
FIG. 8A is an illustration of a pair of oppositely-wound coils of a type suitable for use as the magnet of the system shown in FIG. 7.
Figure 8B:
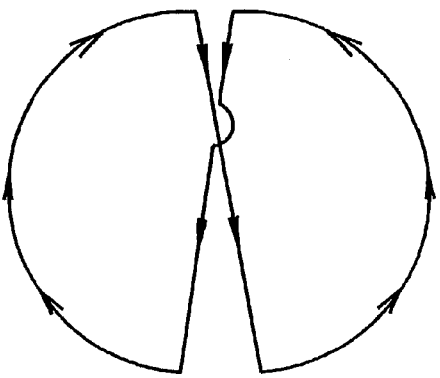
FIG. 8B is an illustration of a single, continuously-wound coil having a cross-over, the coil being of a type suitable for use as the magnet of the system shown in FIG. 7.
Figure 9:
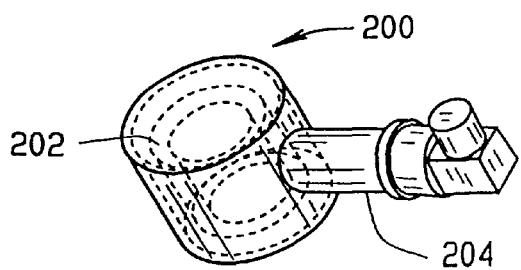
FIG. 9 is a perspective view of a superconducting coil and refrigerator combination.
Figure 10:
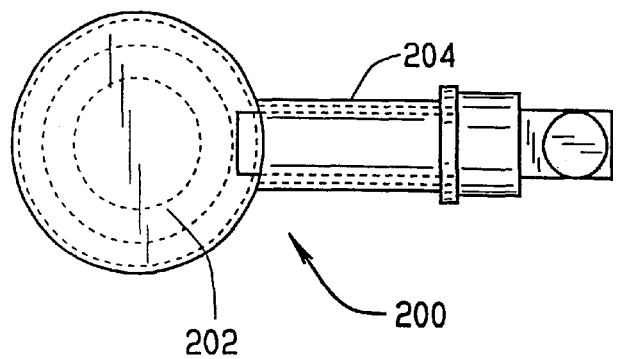
FIG. 10 is a top elevation view of the superconducting coil and refrigerator combination.
Figure 11:
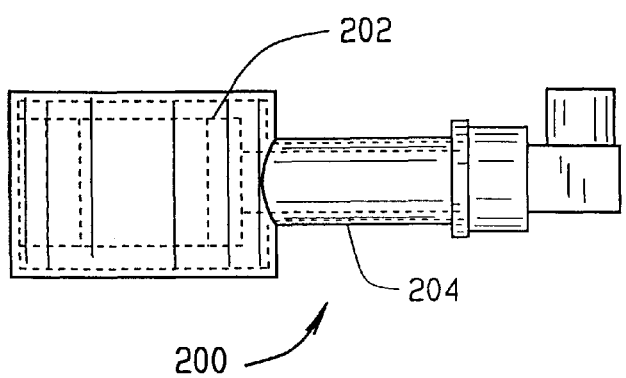
FIG. 11 is a side elevation view of the superconducting coil and refrigerator combination.
Figure 12:
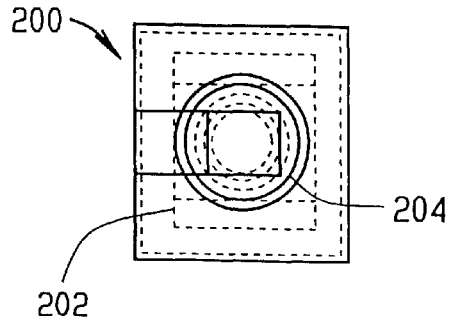
FIG. 12 is an end elevation view of the superconducting coil and refrigerator combination.

Coils 112 and 114 are oppositely wound, as shown in FIG. 8A, or a single, continuously-wound coil 112' with a crossover, as shown in FIG. 8B, may be provided instead. Either of these coil arrangements will operate as a quadrupole magnet to generate transverse gradients, i.e., gradients having a pulling direction perpendicular to the direction of the magnetic field. The field and gradient of the electromagnetic quadrupole magnet 12' are similar in form to those of permanent magnet 12 shown in FIG. 1. An advantage of the permanent magnet quadrupole over a superconducting quadrupole electromagnet is that it is not necessary to provide cryogens for a permanent magnet. However, superconducting coils can have considerably greater strength for a given size and weight. If magnet 12' in FIG. 7 were superconducting, a cryogenic system (not shown) would have to be supplied. The design of a suitable cryogenic system could be accomplished by one skilled in the art, however, and is not considered part of the present invention.

Aside from the stronger magnetic fields obtainable from a superconducting quadrupole electromagnet, another advantage of an electromagnetic quadrupole magnet 12' is that the field strengths produced in the operating region of a patient may be controlled not only by repositioning magnet 12', but by controlling the currents in its coil 112' or coils 112 and 114. This reduces somewhat the need for movement of magnet 12' and possibly the need for certain types of articulation of articulated arm 116.

Although articulated arm 116 is shown in FIG. 7 as being suspended from a ceiling, it will be recognized that other mounting configurations that provide for stable movement and positioning of magnet 12' are also suitable. Also, it should be noted that other configurations of electromagnets that are effective in producing or emulating a multipolar magnetic field (i.e., one of more than 2 poles) may be used instead of the quadrupole example shown and described here. For example, an eight-pole electromagnet could be compactly formed from four coils wound in 90° pie-shaped sections assembled in a circular arrangement. However, absent special circumstances, a quadrupolar field should suffice for surgical applications. (It should be mentioned that a D-shaped section may be considered as a 1800 pie-shaped section.) As shown in FIGS. 9–13, a superconducting coil and refrigerator combination 200 can be constructed for use in magnetically assisted surgery. The combination 200 comprises a superconducting electromagnetic coil 202 and a refrigerator 204. The refrigerator 204 is more compact than the cryogen systems typically used with superconducting magnets, making it possible to bring the superconducting electromagnetic coil closer to the patient without interference from the patient or surrounding medical and imaging equipment. The refrigerator 204 is also not restricted in the orientation in which it can be placed as were prior cryogen systems, allowing more freedom to position and orient the coil and refrigerator combination relative to the patient. A suitable superconducting coil and refrigerator combination 200 may be a Cryofree™ magnet system available from Oxford Instruments, Concord, Mass.

The mechanical refrigerator 204 is preferably attached to one side of the coil 202, with its axis perpendicular to the axis of the coil. Because of the axial symmetry of the coil, its magnetic field and gradients are identical on any circles about the coil axis in planes perpendicular to the axis). At least 270° of such a circle are free of the refrigerator 204, and therefore useful in applying a field to the operating region of the patient without the refrigerator interfering with the patient or other medical or imaging equipment near the patient. Furthermore because of this symmetry the field direction can be reversed or its angle changes by rotation about an axis perpendicular to the axis of the coil, without changing the current in the coil (and its attendant ramp times).

Figure 14:
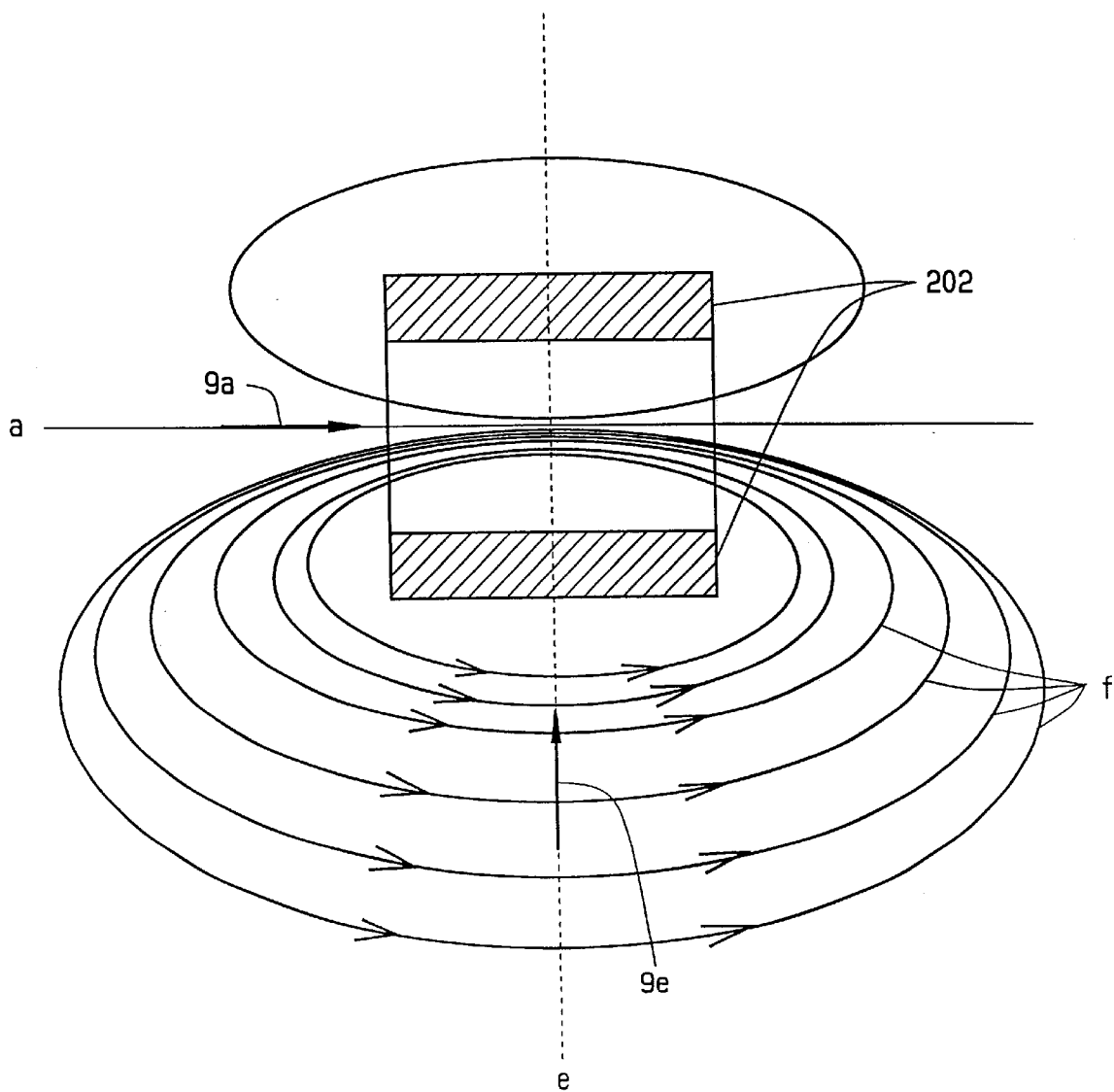
FIG. 14 is a longitudinal cross sectional view of an electromagnet coil showing the field lines and direction of magnetic gradient.

In some applications it is desirable to be able to pull a magnetic device perpendicular to its axis, for example a catheter or electrode having a small cylindrical magnet attached to its distal end. FIG. 14 shows the magnetic field lines surrounding an electromagnetic coil 202, and the direction of the magnetic gradient g. The field lines in the equatorial plane e of the coil 202 are parallel to the axis a of the coil, and thus would tend to align a magnetic medical device in a direction parallel to the axis of the magnet; but the gradient at the equatorial plane $g_e$, is perpendicular to this direction, and will pull a magnetic medical device toward the coil axis. In contrast the gradient along the axis $g_a$ is generally parallel to the field direction, and will pull a magnetic medical device along the axis.

Figure 13:
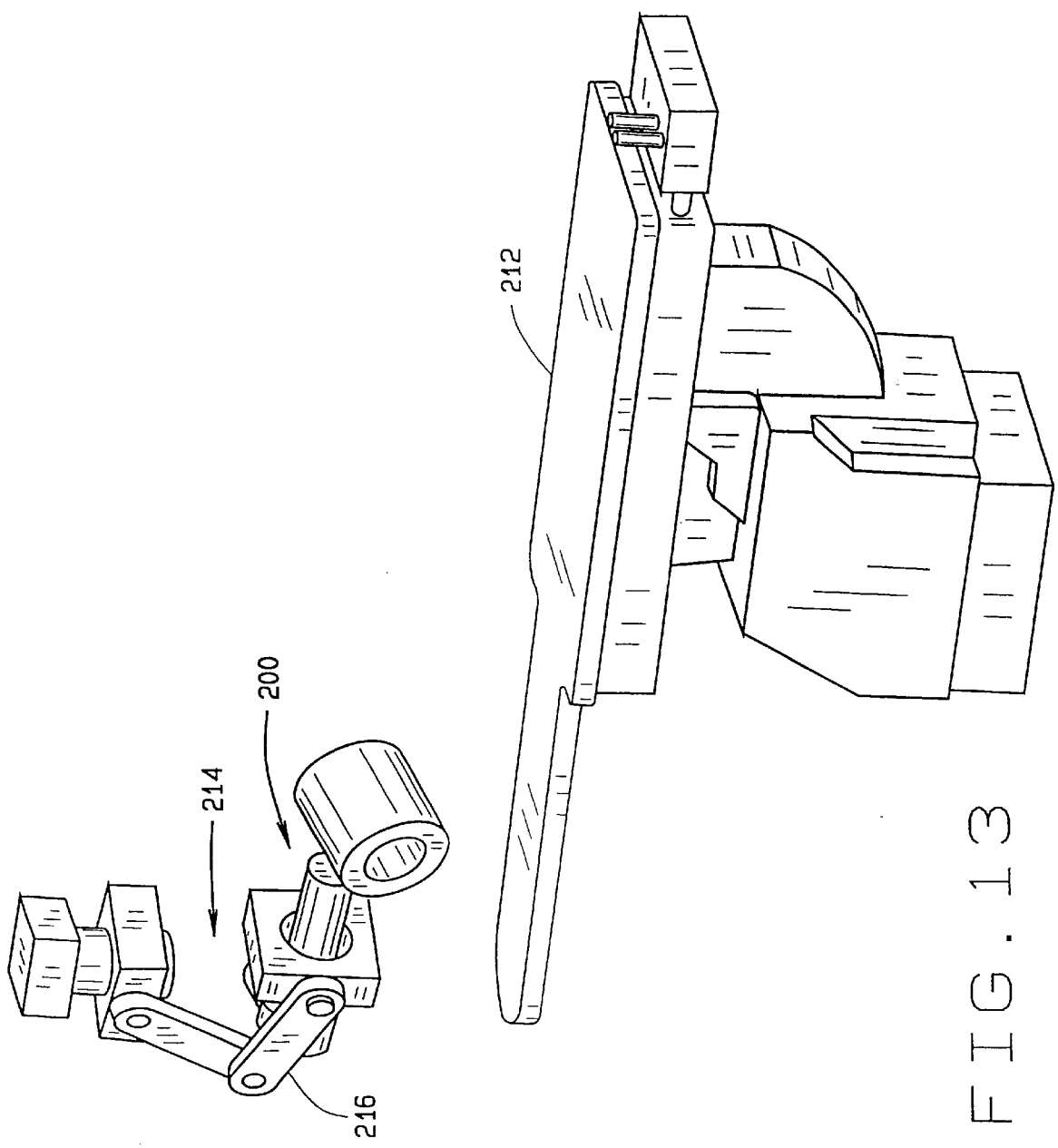
FIG. 13 is a perspective view of a magnetic surgery system including a superconducting coil and refrigerator combination.

As shown in FIG. 13, a superconducting coil and refrigerator combination 200 can be incorporated as part of a magnetic surgery system 210. Magnetic surgery system 210 comprises a patient support 212 for supporting a patient thereon and a magnetic support 214 for moveably supporting the coil and refrigerator combination.

The magnet support 214 is shown mounted on the ceiling, but could also be mounted on the floor. The magnet support 214 has a pivotally mounted articulated arm 216 which can extend and retract to position the magnet coil 202 around the patient to create the desired magnetic field within an operating region in the patient. The magnet support 214 can either be manually operated by the physician, or it can be automatically operated by a computer control which operates one or more motors or actuators to automatically position the magnet in a selected position, or to automatically position the magnet to achieve a selected field or gradient The superconducting electromagnetic coil and refrigerator combination 200 is lightweight and compact to facilitate the manipulation of the magnet with the articulated arm 216.

It will be understood that embodiments incorporating subsets of the inventive concepts herein disclosed are possible that provide some but not all of the advantages of the invention or that meet or satisfy one or more but not all of the objects of the invention. In addition, many modifications of the inventive embodiments disclosed herein will be apparent to those of ordinary skill in the art. Therefore, the scope of the invention should be determined as provided by the claims below, including the full range of equivalents provided under applicable laws.

What is claimed is:

1. A device for magnetically assisted surgery of a patient comprising:

a magnet support structure;

a quadrupole permanent magnet attached to the magnet support structure so that the magnet provides a near-field magnetic field in an operating region within a patient, the magnet being moveable to alter a direction of magnetic field lines in the operating region within the patient, the magnet being generally cylindrical, having a radius and an axis perpendicular to the radius, the magnet comprising a pair of essentially semicircular segments joined so that the segments attract each other and provide, in a region proximate the magnet disk, a magnetic field essentially parallel to the magnet disk along the axis of the magnet.

2. The device of claim 1 wherein the magnet is mounted rotatably on its axis so that a direction of magnetic field lines in the operating region of the patient may be varied.

3. A device for magnetically assisted surgery of a patient comprising:
   a magnet support structure;
   a quadrupole, permanent magnet having at least four poles, the magnet attached to the magnet support structure so that the magnet provides a near-field magnetic field in an operating region within a patient, the magnet being moveable to alter a direction of magnetic field lines in the operating region within the patient, the magnet being generally cylindrical and having a radius and an axis perpendicular to the radius, and being mounted rotatably on its axis so that a direction of magnetic field lines in the operating region of the patient may be varied, and translatably in at least one radial direction.

4. The device of claim 3 wherein the magnet is mounted so that it is translatable in a plurality of radial directions.

5. The device of claim 4 and further comprising a medical imaging system configured to provide a medical image of the operating region of the patient.

6. The device of claim 5 wherein the magnet has at least one face, and wherein the medical imaging system comprises an x-ray source and an x-ray imaging plate on opposite sides of the operating region of the patient, and further wherein the x-ray source and x-ray imaging plate are positioned in a region entirely on one side of a face of the magnet.

7. A device for magnetically assisted surgery of a patient comprising:
   a magnet support structure;
   a quadrupole magnet having at least four poles, the magnet attached to the magnet support structure so that the magnet provides a near-field magnetic field in an operating region within a patient, the magnet being moveable to alter a direction of magnetic field lines in the operating region within the patient, the magnet having a composition.

8. The device of claim 7 wherein the magnet has a 44 MgOe maximum energy product.

9. The device of claim 8 wherein the magnet is disk-shaped and has a radius of about 12.39 inches and a thickness of 6.20 inches.

10. The device of claim 9 wherein the magnet has a generally at least one face, and wherein the magnet provides a field of at least about 0.15 Tesla at 6 inches from its face.

11. A device for magnetically assisted surgery of a patient comprising:
    a magnet support structure;
    a magnet, comprising at least a pair of separately wound electromagnetic coils, the coils each shaped in the form of a pie section and assembled into a circular configuration, the magnet having at least four poles and being attached to the magnet support structure so that the magnet provides a near-field magnetic field in an operating region within a patient, the magnet being moveable to alter a direction of magnetic field lines in the operating region within the patient.

12. The device of claim 11 wherein the pair of separately wound electromagnetic coils are D-shaped, with a flat portion of each of the D-shaped coils adjacent one another.

13. The device of claim 11 wherein at least one of the electromagnetic coils is superconducting.

14. The device according to claim 13 where at least one superconductor coil has a mechanical refrigerator associated with it for maintaining the superconducting state of the superconducting magnet coil.

* * * * *